US006550471B2

(12) United States Patent
Szymocha et al.

(10) Patent No.: US 6,550,471 B2
(45) Date of Patent: Apr. 22, 2003

(54) HEATED CLOTHING FOR USE IN COLD WEATHER AND COLD CLIMATE REGIONS

(75) Inventors: Kazimierz Szymocha, Edmonton (CA); Tad Sudol, Edmonton (CA)

(73) Assignees: Alberta Research Council, Inc., Edmonton (CA); Technology & Research Incorporated, Edmonton (CA)

(*) Notice: Subject to any disclaimer, the term of this patent is extended or adjusted under 35 U.S.C. 154(b) by 65 days.

(21) Appl. No.: 09/865,261

(22) Filed: May 25, 2001

(65) Prior Publication Data

US 2002/0029410 A1 Mar. 14, 2002

(51) Int. Cl.[7] .............................. A61F 7/00; A61F 7/08

(52) U.S. Cl. ....................................... 126/208; 126/204

(58) Field of Search ................................ 126/204, 207, 126/208; 36/2.6

(56) References Cited

U.S. PATENT DOCUMENTS

| | | | | |
|---|---|---|---|---|
| 3,999,037 A | | 12/1976 | Metcalf, Sr. | |
| 4,404,460 A | | 9/1983 | Kerr | |
| 4,547,906 A | * | 10/1985 | Nishida et al. | 2/93 |

(List continued on next page.)

FOREIGN PATENT DOCUMENTS

| | | | |
|---|---|---|---|
| CA | 410063 | 1/1943 | |
| CA | 2295261 | 1/2000 | H05B/3/36 |
| CA | 2306029 | 4/2000 | H05B/3/54 |

(List continued on next page.)

OTHER PUBLICATIONS

Abstract of U.S. Patent No. 5,032,705, Batcheller et al., Issued Jul. 16, 1991.

Abstract of U.S. Patent No. 5,777,296, Bell, Issued Jul. 7, 1998.

Abstract of U.S. Patent No. 3,744,053 Parker et al., Issued Jul. 10, 1973.

(List continued on next page.)

*Primary Examiner*—Henry Bennett
*Assistant Examiner*—Alfred Basichas
(74) *Attorney, Agent, or Firm*—Davis & Bujold, P.L.L.C.

(57) ABSTRACT

The claimed invention relates to an heated clothing with autonomous heating source and comprise (a) thermally insulated suit adapted to cover the human body, (b) portable, low-temperature heat generation module with combustion process controlled by a control unit, c) infrared window for energy delivery, (d) heat energy distribution system to supply heat to different parts of the body, (e) temperature control system, including the temperature sensors, responsible for maintaining proper temperatures at different parts of the body and f) moisture adsorbing pads to remove excessive moisture originating from sweating. A light and flexible suit provides controllable stream of heat from a heater to a wearer for prolonged time. The suit includes attachable, heated gloves and boots and gives complete protection against even extreme cold. The invention can find application in the protection of people being exposed to cold environment, including construction workers, mineral exploration and oil field personnel, and other employees who's jobs require them to work at adverse weather conditions or those exposed to cold surroundings. It is also applicable for sport, pleasure and other recreational purposes. The heat generated by low-temperature heating unit, that is portable but located outside of the suit, is transferred to the interior of the suit via special window by means of infrared radiation. Infrared radiation energy is absorbed by the heat collecting plate and transferred inside of the suit to the different parts/regions of the human body by a heat distribution system. The control system module is equipped with temperature sensors, to measure temperature of different parts of the wearer's body, and provides for the control of stream of heat delivered to particular part of the body. The temperature of body parts is kept in the preset limits of temperature set individually by the suit user.

37 Claims, 14 Drawing Sheets

U.S. PATENT DOCUMENTS

| | | | | | |
|---|---|---|---|---|---|
| 5,008,517 | A | | 4/1991 | Brekkestran et al. | |
| 5,269,369 | A | | 12/1993 | Faghri | |
| 5,879,378 | A | * | 3/1999 | Usui | 607/96 |
| 6,215,111 | B1 | | 4/2001 | Rock et al. | 219/545 |
| 6,307,189 | B1 | | 10/2001 | Rock et al. | 219/545 |

FOREIGN PATENT DOCUMENTS

| | | | |
|---|---|---|---|
| CA | 2350364 | 6/2001 | H05B/3/20 |
| DE | 1610647 | 10/1965 | |
| FR | 78 28439 | 10/1978 | |
| JP | 11050314 | 2/1999 | |

OTHER PUBLICATIONS

Abstract of U.S. Patent No. 4,024,730, Bell et al., Issued May 24, 1977.

Abstract of U.S. Patent No. 4,146,933, Jenkins et al., Issued Apr. 3, 1979.

Abstract of U.S. Patent No. 4,914,752, Hinson et al., Issued Apr. 10, 1990.

Abstract of U.S. Patent No. 4,691,762, Elkins et al., Issued Sep. 8, 1987.

U. S. patent application No. 09/761,791, Electric Resistance Heating/Warming Fabric Articles, Rock et al., filed Jan. 17, 2001.

U. S. patent application No. 09/791,237, Electric Heating/Warming Fibrous Article, Rock et al., filed Feb. 23, 2001.

U. S. patent application No. 09/814,896, Electric Heating/Warming Fabric Articles, Rock et al., filed Mar. 22, 2001.

* cited by examiner

HEATED CLOTHING FOR USE IN COLD WEATHER AND COLD CLIMATE REGIONS

BACKGROUND OF THE INVENTION

The present invention relates to a new type of heating suit that is useful for a different types of activities including working, rescue missions, recreation or sport activities in adverse weather conditions, in extreme low temperature environments or for medical treatment. Protection of the people from extremely cold environments in certain regions is of significant practical importance. The heating suit as described, with a powerful, portable and light heat source and very sophisticated heat control and distribution system, for a first time gives a human unlimited freedom to stay outdoor for prolonged time even at extreme cold weather conditions.

Heated clothing first appeared during the First World War as a mean of keeping the aircraft pilots warm and mostly applied an electric energy for heating purposes.

In the prior art there are many different types of heated garments applied for outdoor use. The most known are garments with the heating systems connected to some stationary equipment used as a source of heat, or garments with electrical heating. In most of this solutions wearer of the heating garment has to be connected to the source of energy by an umbilical cords or electrical cables and as a result of this connection his mobility is very limited.

The closest prior art solution known is a garment disclosed in Japanese Patent No. 11050314 (Desanto). According to this solution the wearer is carrying a self-contained heating unit connected with a warming jacket by hot gas passages. The main disadvantage of this solution is that only limited portion of body (upper torso) is heated as a lack of the heat distribution system. Another problem related is condensation of the water vapors originating from the hydrogen combustion process inside of a warming jacket.

Another class of garments known is electrically heated clothing. Examples of this type of garment are described in the following patents: Canadian Patent No. 0410063 (Taylor), U.S. Pat. No. 3,999,037 (Metcalf), U.S. Pat. No. 4,404,460 (Kerr), U.S. Pat. No. 5,008,517 (Brekkestran), U.S. Pat. No. 5,032,705 (Batcheller), U.S. Pat. No. 5,777,296 (Bell). The electrically heated clothing requires to be connected to the electricity source by cables or to be equipped with battery package that often is heavy, cumbersome and with a relatively short life. Both of these solutions have significant disadvantages. Presently this sort of clothing mainly is offered for motorcycle users, for people with cold jobs or disabled people in wheelchairs.

Another type of heating/cooling garments which was distinct in the prior art relay on application of heat delivered from outer source of heat (e.g. engine). The heating garment in this case is connected with heat source by conduits or pipes. The heat is delivered by forced circulation of the heat transmission fluid (gas or liquid). Examples of such apparatus are shown in German Patent No. P 1610647.1 (Holzer), that describe a heat exchanger system arranged inside of the suit with flexible fluid hoses connected to external source of heat, and French Patent No FR 2,437,973 (Bidou) that uses hot air drown from another source of heat (e.g. engine) and blown through channels in protective clothing. Other similar patents based on fluid circulation systems are: U.S. Pat. No. 3,744,053 (Parker), U.S. Pat. No. 4,024,730 (Bell), U.S. Pat. No. 4,146,933 (Jenkins), U.S. Pat. No. 4,914,752 (Hinson), U.S. Pat. No. 5,269,369 (Faghri). However, the disadvantages of these known warming garments is that they are connected by conduits or pipes to a usually stationary heat generating units and wearer mobility is very limited. These garments are cumbersome (thick when inflated) or heavy and rigid mostly because of extensive heat exchange fluid circulation systems. These garments are not equipped with any heat distribution control systems allowing actively and independently control the temperature of different parts of the body.

SUMMARY OF THE INVENTION

It is a principal object of the invention to provide a very efficient, lightweight, equipped with its own source of energy, selectively heated clothing for use in adverse, cold weather conditions.

A further object of the present invention is that the warming suit allows staying outdoors for prolonged (practically unlimited) time, is not obstructing movements and has unlimited range of mobility.

The heated clothing according to this invention is based on an innovative concept that utilizes a light, portable, low-temperature heating unit as a source of heat, and heat distributing system that selectively delivers heat to different parts of the body. The heated clothing is equipped with a monitoring and control system that respond according to ambient conditions and maintain a balanced body temperature and moisture.

This heated clothing is light, comfortable and energy efficient. It may be regarded as a garment for work purposes or optional dress for warmth without the bulk. The suit includes attachable, heated gloves and heated boot inserts.

There is no need for any connecting cables (see prior art) or moving machines thus the person wearing the suit can move freely and cost of operation are very low.

This invention includes devices, materials and methods for providing a heated suit with a system that allows keep balanced body temperature. The warming suit is furnished with heat distribution system and microclimate control system that responds actively and easy adapt to the changing surrounding conditions and gives possibility to distribute the heat to different parts of the body accordingly to individual needs of the wearer. Additionally, the suit is equipped with the moisture absorption pad to remove excessive moisture (sweating) inside of the clothing.

The purpose of heated suit is to keep a person comfortably warm, during the outdoor activity, The heated clothing according with this invention is expected to let people perform any outdoor job for prolonged periods of time, even at extremely cold weather conditions (down to minus 40° C.), during long winter seasons in cold climate regions (northern Canada or any other cold climate region in the world). It is the principal object of this invention to overcome the mentioned prior art disadvantages by implementation of the very efficient, portable and light heat source, and by that free people from any connections to the stationary heat delivery systems limiting of the wearer mobility.

The object of the present invention is thus to provide an improved very light, flexible and autonomic warming suit, in particular for anybody who wont to protect himself against undesirable external cold influences, while simultaneously maintaining easiness to move, freedom to relocate and possibility to control the temperature of each part of the body independently. The applied heating distribution system is arranged in such a way that it may be adapted, in terms of the heat distribution, to individual needs of the wearer. The whole system is very reliable, energy efficient (there is no any moving machines) and as result the cost of operation are very low.

The heated clothing according to this invention is regarded as a major step towards future "smart clothes" that is expected to provide new level of comfort, functionality and convenience for a wearer.

An object of the present invention is the suit in a form of an overall, that is made of weather resistant fabric characterized by very good thermal insulation characteristic and equipped with slots and pockets to accommodate required equipment. The internal side of the suit is covered with attached network of heat distribution lines.

Another object of invention is an heat generation and transmitting system comprising a flame-less, low temperature source of heat, that is portable, preferably propane heater, the window transparent for infrared radiation and the heat collecting plate absorbing infrared radiation. The small size of the catalytic heater with heating power in the range from 50 to 500 watts is located in a special pocket situated on back of the body. The pocket is equipped with air intake and exhaust slots to facilitate access of air required for combustion process. The combustion products in form of off-gases are discharged to the atmosphere. The heater's surface, with a temperature in the range from about 200° C. to 450° C., generates the infrared radiation energy that is transferred to the collecting plate located inside of the suit via an infrared window. The collecting plate adsorbs radiation energy and distributes it to the different regions of the body. The infrared window separates the suit interior (hot) space by means of barrier (membrane) from the heater and surrounding (cold) atmosphere.

A further object of the invention is a heat distribution system that consists of arrangement of shatters or valves and transmitting lines used to distribute heat to different parts of the body. Although any suitable method may be used to transfer the heat to the collecting plate and further distribute the heat from the collecting plate to different parts of the human body, as described above, the heat transfer is preferably performed in accordance with two methods of the within invention.

In a first embodiment heat distribution method consists of the collecting plate, absorbing infrared energy, and comprises a system of optical fibers with connections to different regions of the human body. The infrared radiation collecting plate is equipped with shatters to control selectively the amount of radiation transmitted to the optic fibers based distribution system.

The heat energy, in a form of infrared radiation, is transferred via fiberoptics channels and released at the end of each fiber, thus heating the targeted region. The fibers are sufficiently thin to be elastic and main transfer lines might be in a form of the flat bundles of fibers (multi-track fiber optic) attached to the suit.

In a second embodiment, the heat distribution system consists of the heat collecting plate, (in a form of the flat heat exchanger with a surface well absorbing infrared radiation) and plurality of small diameter fluid channels arranged in networks transferring heat to the different regions of body. The fluid circulation might be forced by different means. An option of the fluid pumping system is a solution that applies diaphragm pumps located in shoes (between heel and shoe) and activated by walking. Control valves control the flow rate through sections of the network. Another option is thermally induced flow (thermal convection) or the micropump forced flow.

A further object of the invention is the temperature control system relying on a number of temperature sensors located in different parts of the body. These temperature-measuring sensors, via control system module, activate the shutters or valves that adjust the stream of energy delivered to the specified locations. The temperatures can be seen and set on control and display module.

Yet another object of the invention is to provide for the removal of moisture (sweat) that is generated especially during physical activity. To keep a person dry and comfortable underneath the excessive moisture is removed by moisture absorption pads located inside of suit. Moisture absorption pads are based on polymers characterized by a very high water absorption capacity.

The novel feature which are considered characteristic for the invention are set forth in the appended claims.

The invention itself, however, both as to its construction and its principle of operation, together with additional objects, features and advantages thereof, will be best understood from the following description of the specific embodiments when read and understood in connection with the accompanying drawings.

BRIEF DESCRIPTION OF DRAWINGS

The above and other objects, features and advantages of the present invention will be better understood from a reading of the following detailed description of preferred embodiments with the accompanying drawings, in which.

DETAILED DESCRIPTION

Suit

Figure 1:
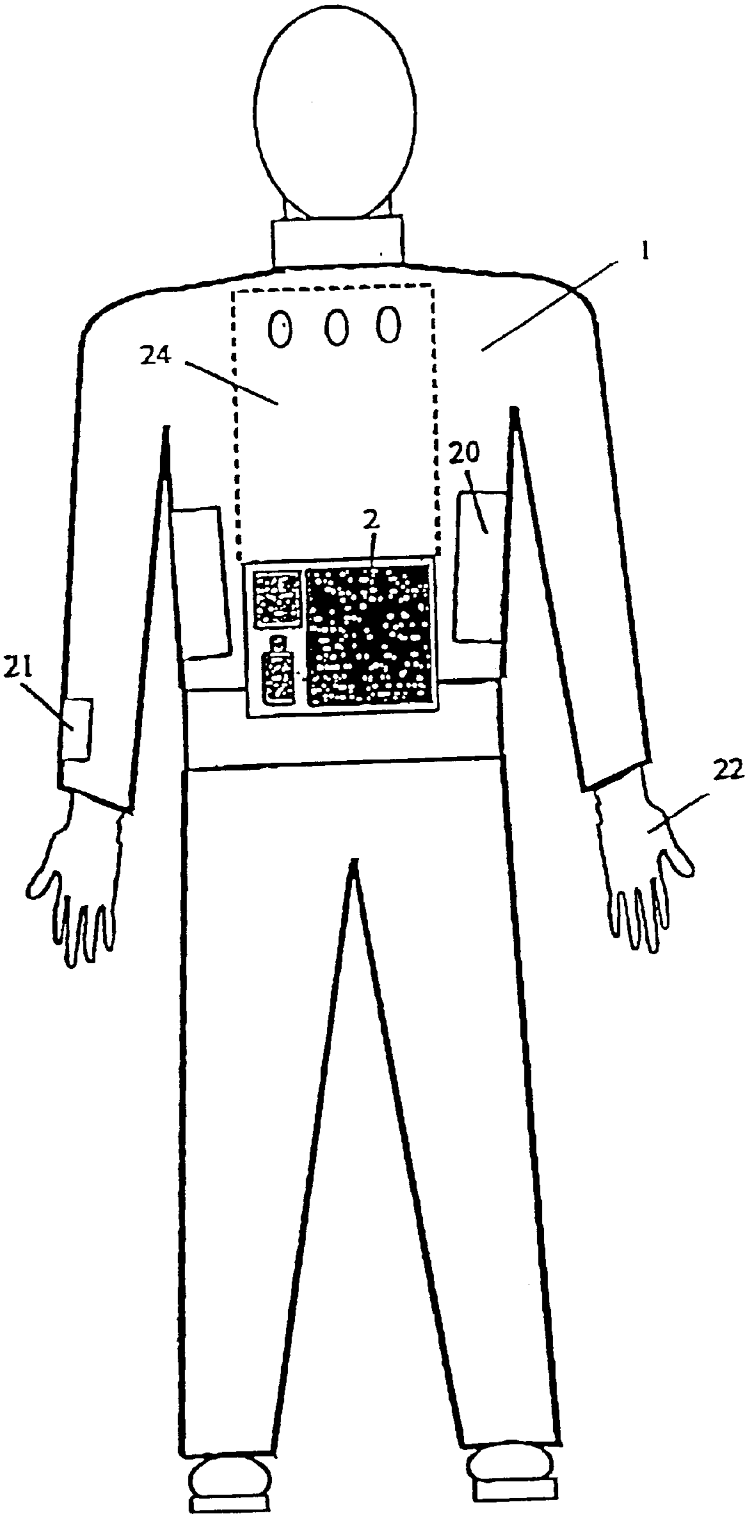
FIGS. 1 and 1A (hereinafter FIG. 1) are a pictorial representation (front and side view) of the preferred heated suit with heating module and moisture adsorption pads that embodies the invention.
Figure 1A:
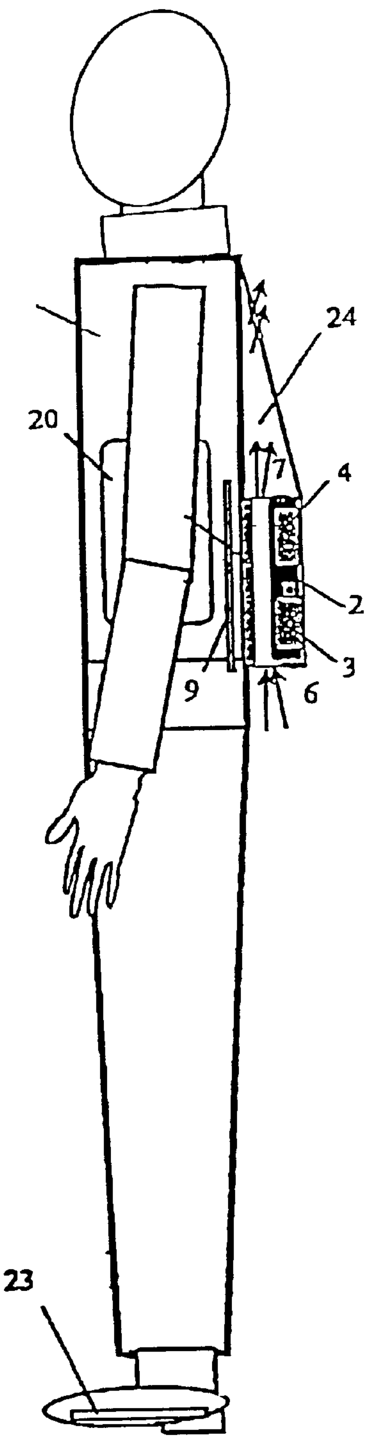

Referring to FIG. 1 a lightweight, weather-proof suit for body protection and heating is shown according to the invention. The suit is equipped large pocket with a frame 13 supporting the attachable heater 2, transmitting window 9, collecting plate 8 and heat distributing lines 10 and 16. Additionally, suit 1 is equipped with additional pockets for housing moisture absorbtion pads 20 and with another pocket, located in an end of one of the sleeves that is predicted for housing a display/control module 21. The suit is designed so that it essentially covers the torso, arms and legs. The warming suit is supplemented by detachable heated gloves and heated shoes insertions. An option for head hood is predicted if required. The suit making outer protective layer/cover is made of good thermal insulating materials that shield off the cold from the environment to the human body. The suit, in a form of a double layer overall 1, is made of fabric recognized for very good thermal insulation characteristic. Any of a variety of materials presently available on the market is suitable for the outer shell. Preferably, suit is maid of a fabric which is durable with water-repellent coatings, lightweight and well heat insulating property (Climawarm™ or combination of Gore-Tex™ and Thinsulate™). The inner layer is normally used cloth or underwear fluid-permeable, accommodated for free air movement and perspiration. The human body temperature can be maintained at a temperature close to normal, regardless of the environment a person encounters. The suit to be used in the human body heating system is light, flexible and do not restrict movements.

Heater

The heated clothing as invented is equipped with an own (autonomic) source of heat that is a very light, flame-less, low-temperature, portable, catalytic gas heater 2, preferably propane-butane or propane heated. The heat is generated as result of low temperature exothermic catalytic reaction of fuel (propane) with oxygen. The catalytic reaction is self-sustaining and will continue until the fuel is shut off to the heater. Low rate of the reaction of the oxidation process in the catalyst ensure that the catalyst does not become an ignition point even when the heater is operating in an explosive atmosphere. The amount of heat generated can be controlled by changing flow rate of fuel delivered to the heater and regulated by thermostat. The products of the reaction are infrared radiation energy, water vapor and carbon dioxide. The infrared heater does not produce harmful carbon monoxide gas when used with propane. The infrared heater operates at range of temperatures of between 200 to 430° C. and generates infrared radiation in the wave range from about 4 to 7 μm. Inside of the heater there is located a thermometer connected to the control module that controls the heater temperature. Depending to a temperature the control module that is connected to a gas control valve, changes gas flow rate in response to the changing demand for heat. The thermal insulation layer covers the outer surface of heater to keep heater hot and prevent unnecessary heat losses.

The infrared heater is commercially available and can be manufactured to obtain any heating power, however, for purpose of the suit heater it is desired to keep it in the range from about 50 to 300 watts.

The infrared heater module can be easily replaced if required. The fuel source is expected to be a propane or propane-butane mixture in 100 g cartridges that can be easily replaced. Typically, one 100 g gas cartridge is expected to be sufficient for about 6 hours of heater operation.

The small size catalytic heater is removable and is located in a special slot of frame 13, together with a fuel supply cartridge 3, on back of the body in the special pocket as shown in FIG. 1. The heater practically may be carried anywhere on the body. However, it is advantageous to carry the heating module over the back. The heater pocket is equipped with air intake 6 to facilitate access of air required for combustion process and heat resistant shield 19 forming a intermediate chamber with exhaust slots 7. The combustion products in form of off-gases, after some heat recovery in the intermediate chamber, are discharged through slots 7 to the atmosphere. The heater surface temperature is in the temperature range from about 200° C. to 450° C. and generates the infrared radiation (3 to 7 μm wavelength). This radiation is transferred to the heat collecting plate 8 located inside of the suit via an infrared window 9 transparent for infrared radiation. The infrared window separates the suit interior space (worm) by means of barrier (membrane) from the heater and surrounding atmosphere (cold), so only infrared radiation can be transferred to the interior of the suit and to collecting plate 8 particularly. The low-temperature catalytic heater used as a heat source in this invention and propane-butane fuel cartridges are commercially available.

Heat Distribution System

The heating suit in accordance with the present invention is equipped with an advanced heat transfer and distribution system. Although any suitable method may be used to transfer the heat from the collecting plate to different parts of the human body, as described above, the heat transfer is preferably performed in accordance with two preferred methods within the invention.

Figure 2:
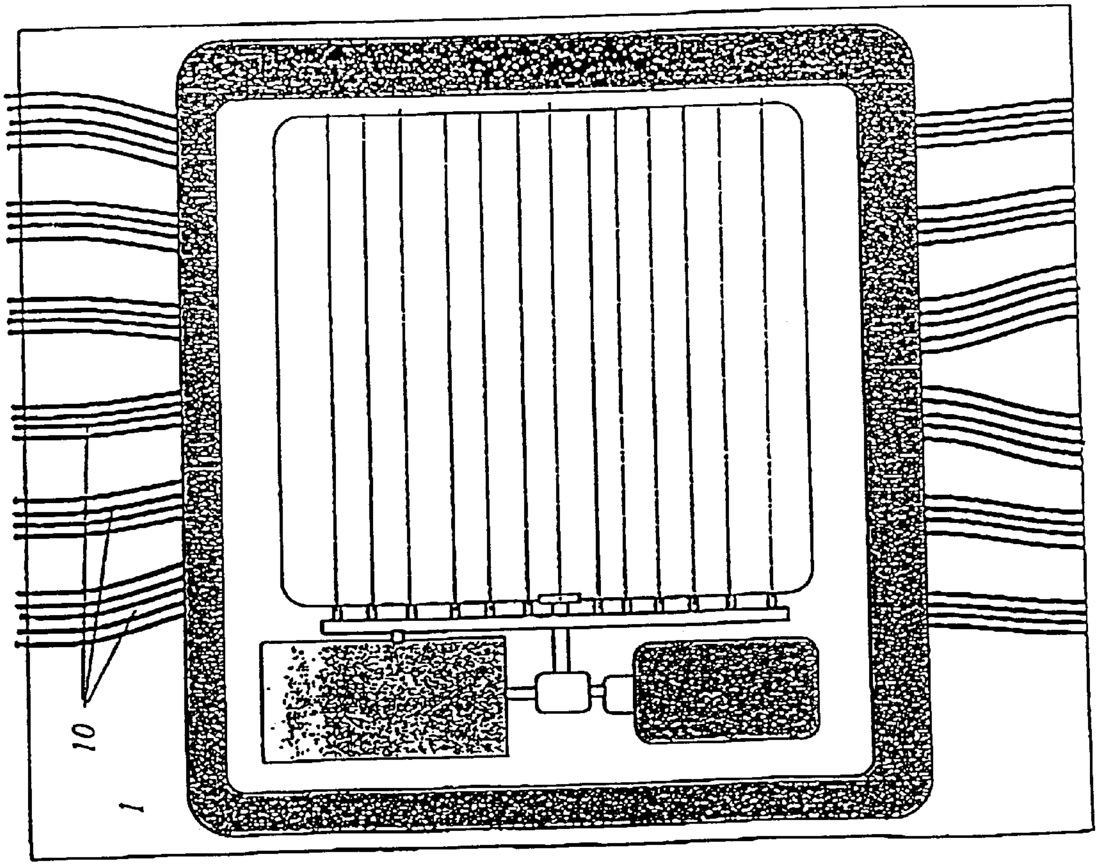
FIGS. 2 and 2A (hereinafter FIG. 2) are showing a cross-sectional view of the heating module in accordance with the first embodiment of the infrared heater, collecting plate and heat distribution system based on optic fibers.
Figure 2A:
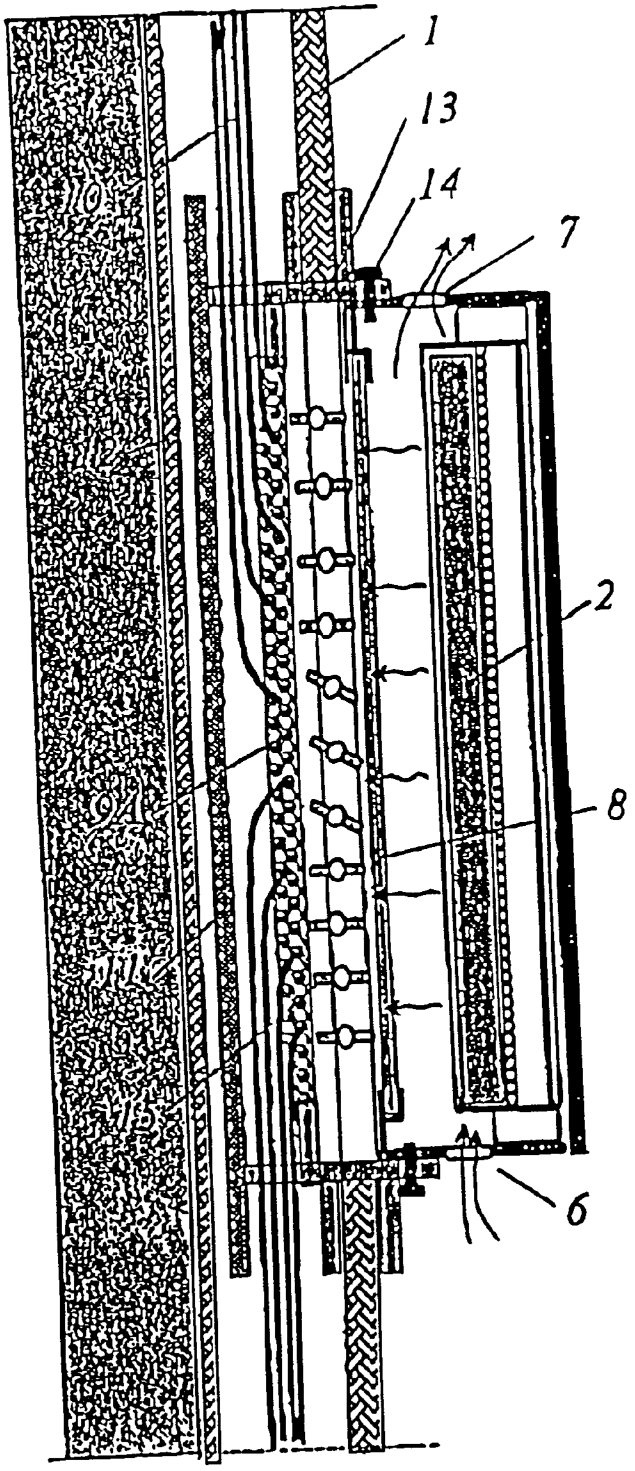
Figure 4:
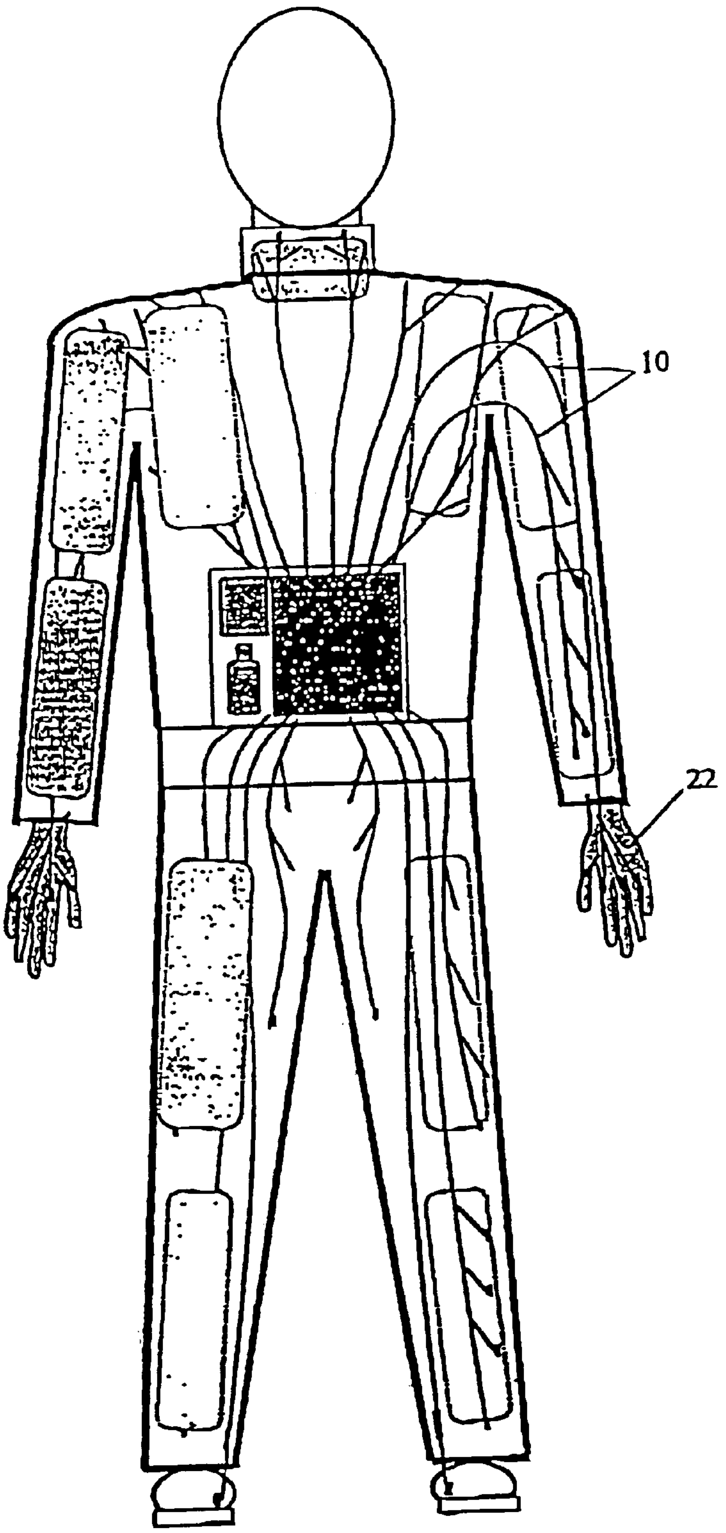
FIGS. 4 and 4A (hereinafter FIG. 4) are presenting a heat distribution system based on infrared radiation collecting plate and fiber optics heat transfer system.
Figure 4A:
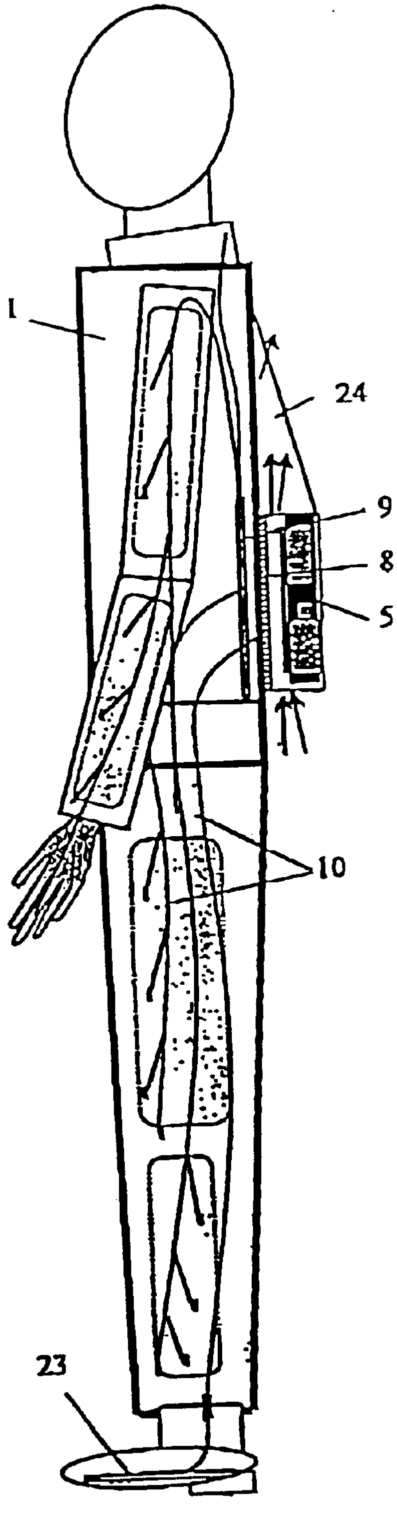

In a first embodiment, shown in FIG. 2 and FIG. 4 the heat distribution system consists of the radiating heater 2, infrared radiation transparent window 9, infrared radiation collecting plate 8 and a network of optical fibers 10 arranged in the bundles, with connections to different regions of the human body. The infrared radiation collecting plate 8A, that in this embodiment is an optical system, is equipped with shatters 15 controlling the stream (intensity) of radiation delivered to the particulate section of the collecting plate. The collecting plate concentrate and direct the infrared radiation into the optic fibers bundles that are energy transferring lines, to different regions of the body. The infrared radiation is released at the end of each fiber equipped in micro-heater, thus heating the predicted region. The fibers are sufficiently thin to be elastic and main transfer lines are in a form of flat bundles of fibers attached to the suit.

Figure 3:
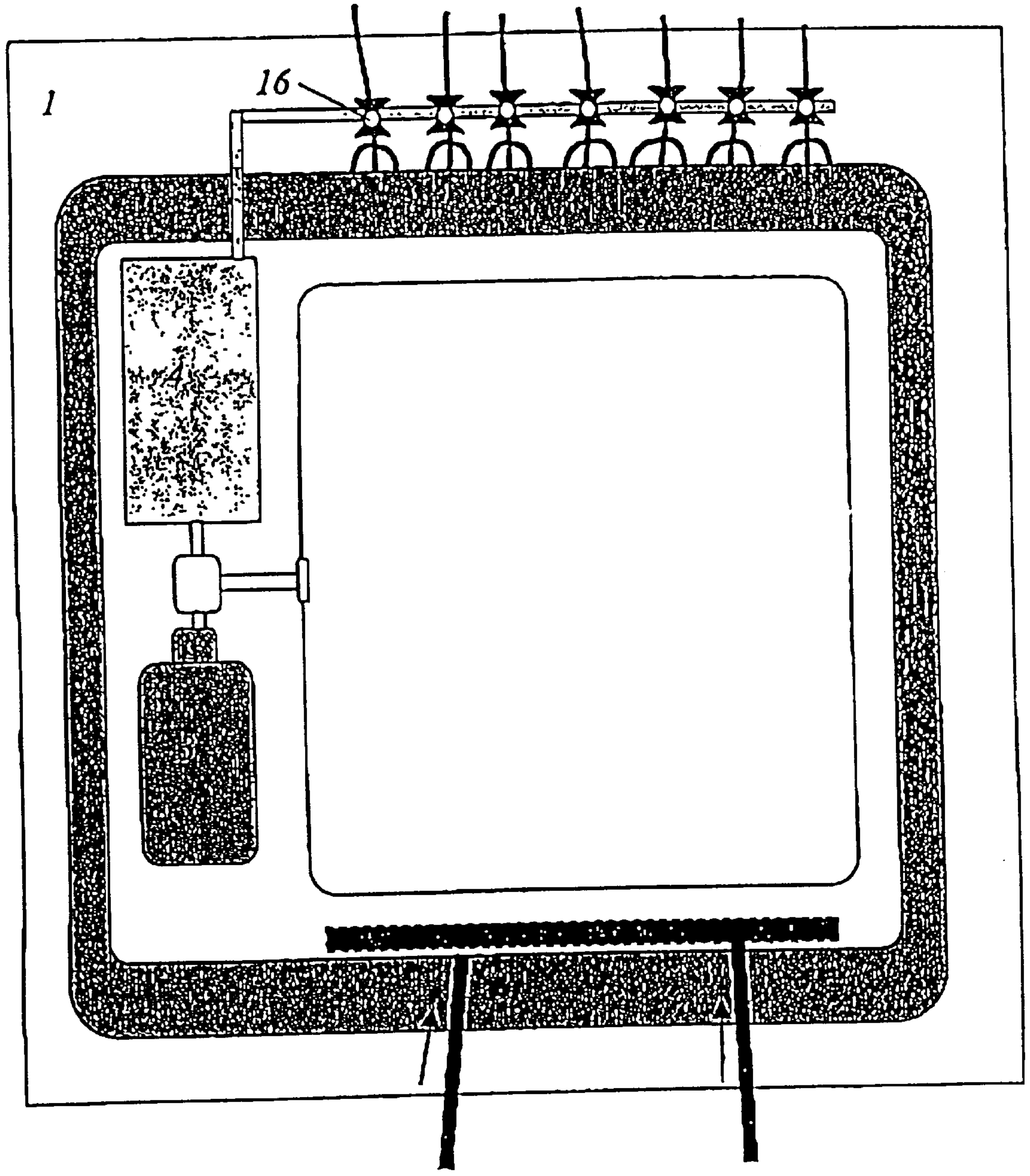
FIGS. 3 and 3A (hereinafter FIG. 3) are showing a view of the heating module in accordance with the second embodiment of the infrared heater, collecting plate and heat distribution system based on heat exchanger and fluid heating lines.
Figure 3A:
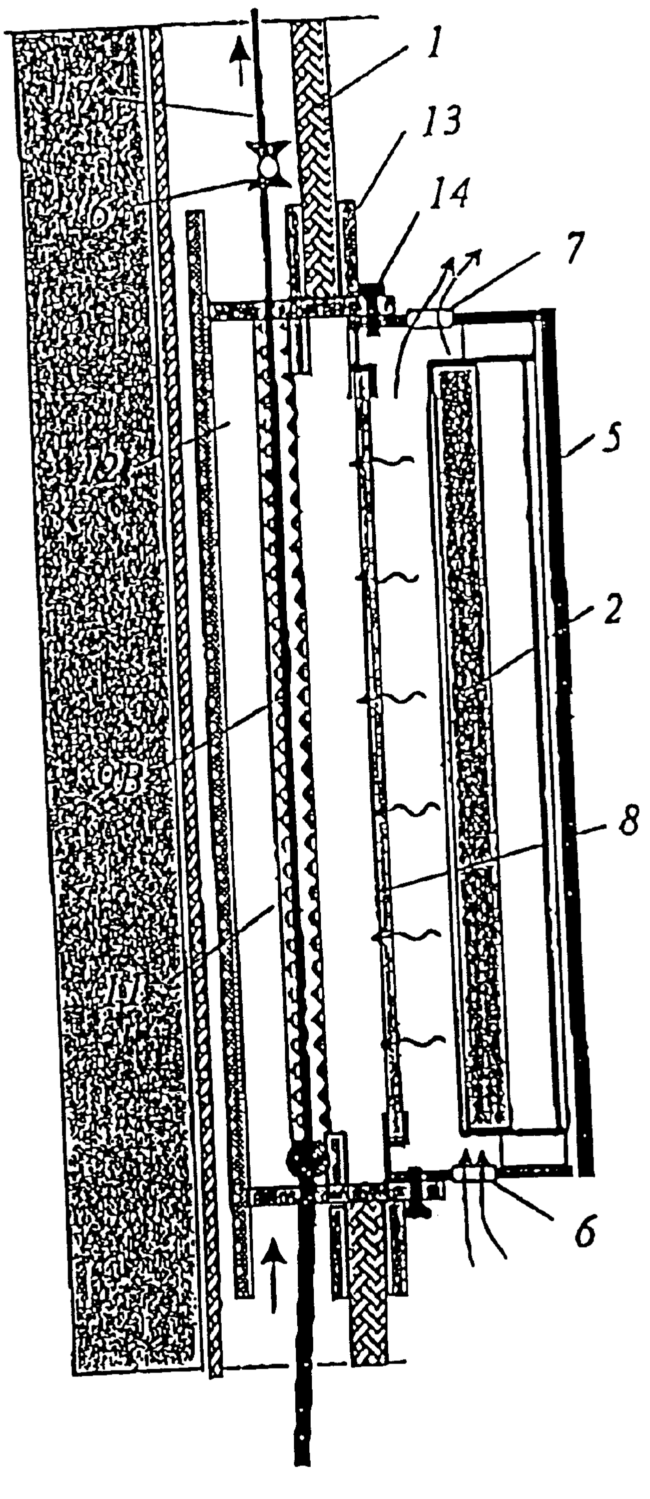
Figure 5:
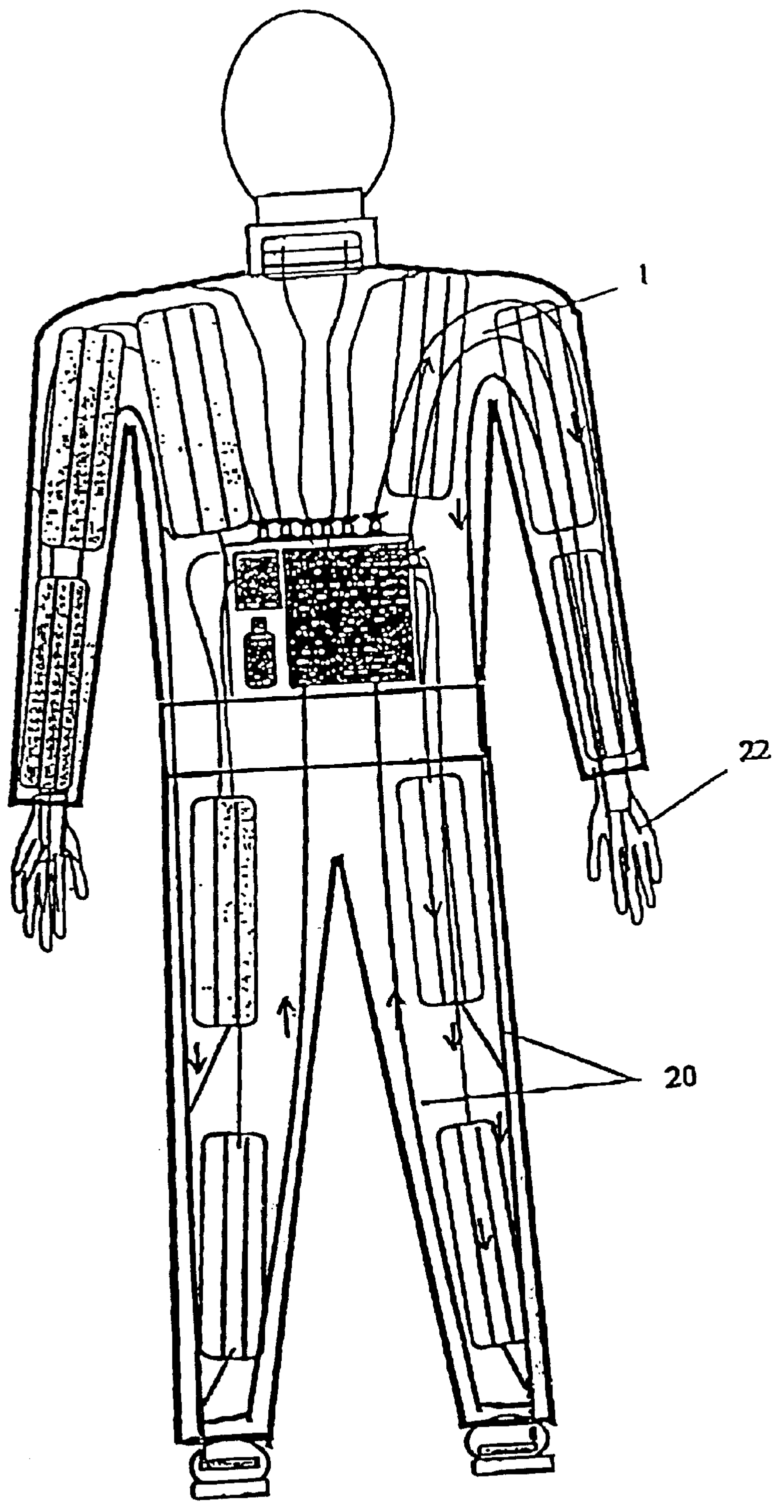
FIGS. 5 and 5A (hereinafter FIG. 5) are showing an alternative heat distribution system based on collecting plate in a form of heat exchanger and a network of channels with circulating fluid.
Figure 5A:
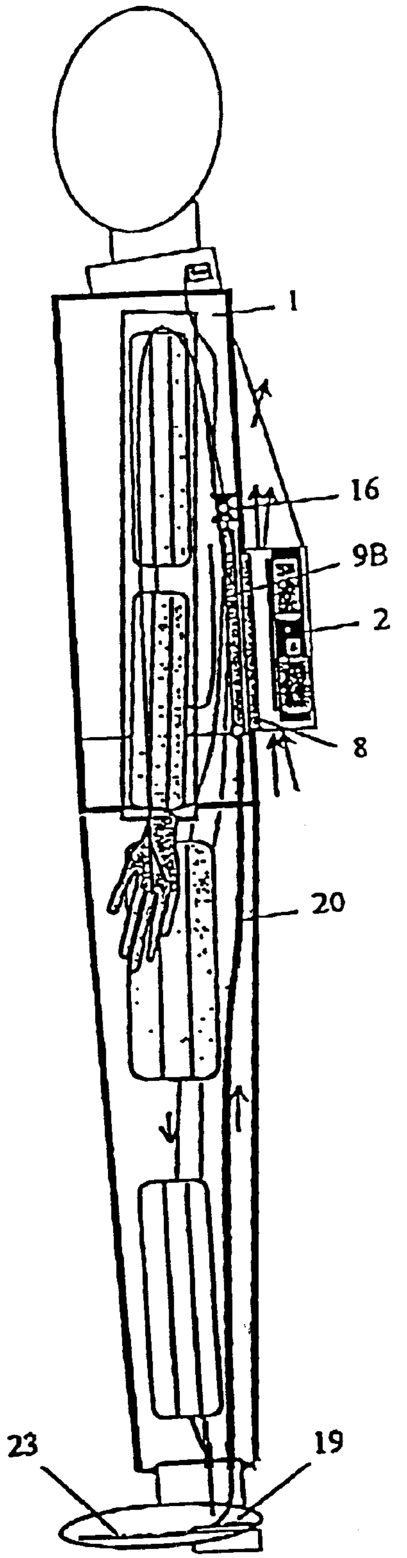

In the second embodiment of the heat distribution system, shown in FIG. 3, and FIG. 5 the infrared radiation from the heater 2 is directed on the heat collecting plate 8 in a form of the flat heat exchanger with surface well absorbing infrared radiation. The plate of the heat exchanger with plurality of small diameter channels divided in sections, absorbs and transforms infrared radiation into heat energy delivered to fluid flowing through these channels. The sections of channels, forming primarily heat exchanger, are connected with individual collectors 16 equipped with individual control valves 17. The rate of flow trough each section, that is connected with different portion of the fluid circulating system located at different part of the body (secondary heat exchangers), is controlled by separate control valve 17. Heat exchanger made of flexible pipes includes plastic smooth or corrugated tubes.

Figure 6:
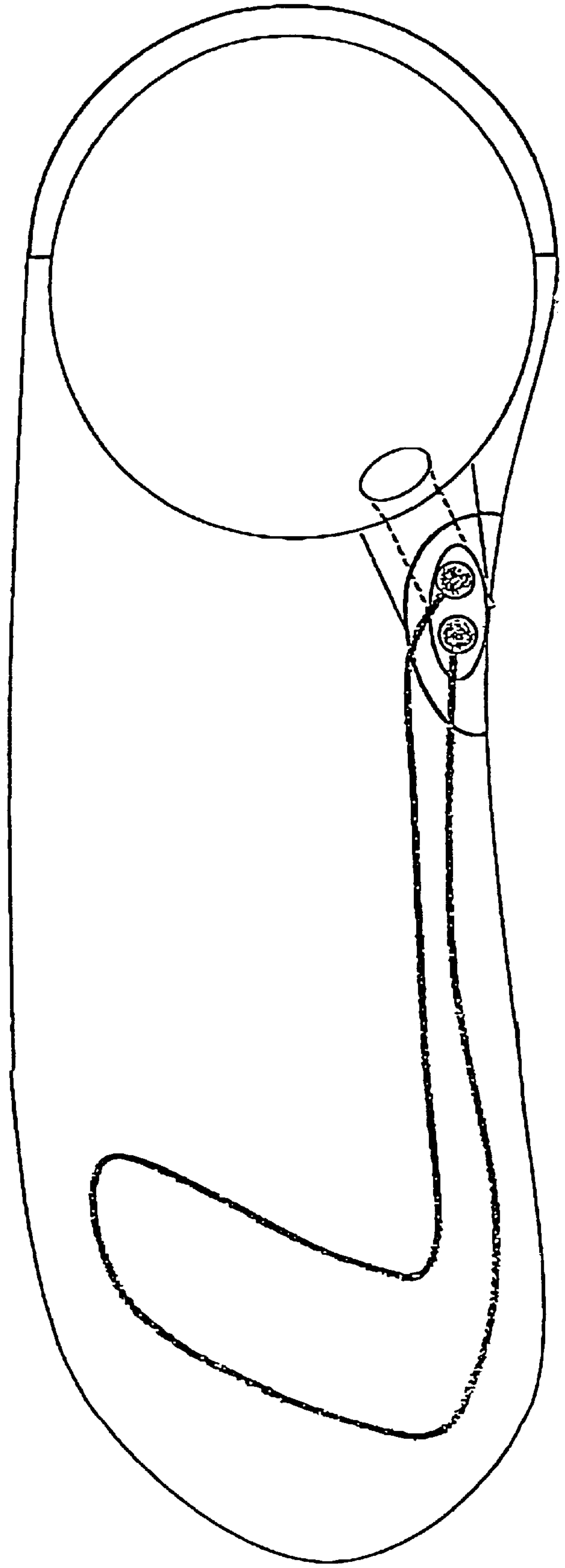
FIGS. 6 and 6A (hereinafter FIG. 6) are presenting a diaphragm pump forcing fluid circulation and activated by walking.
Figure 6A:
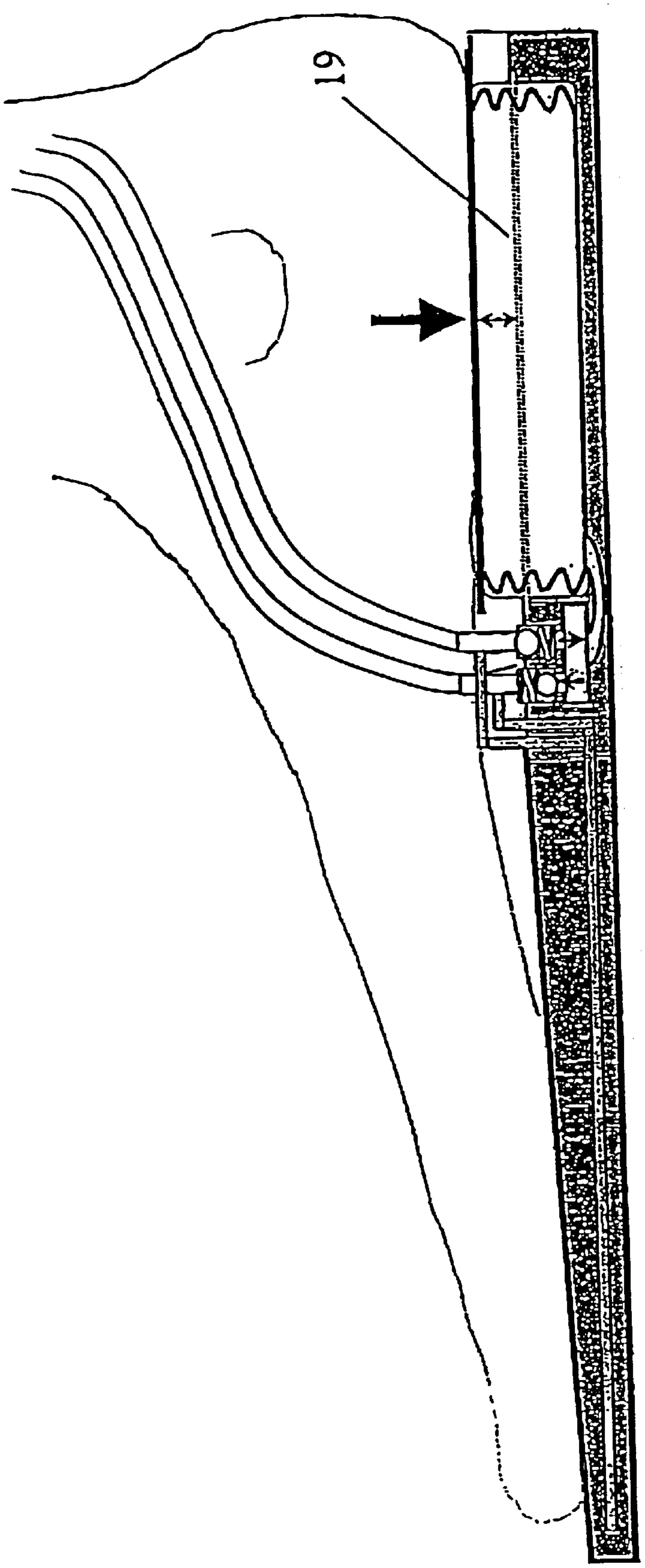
Figure 7:
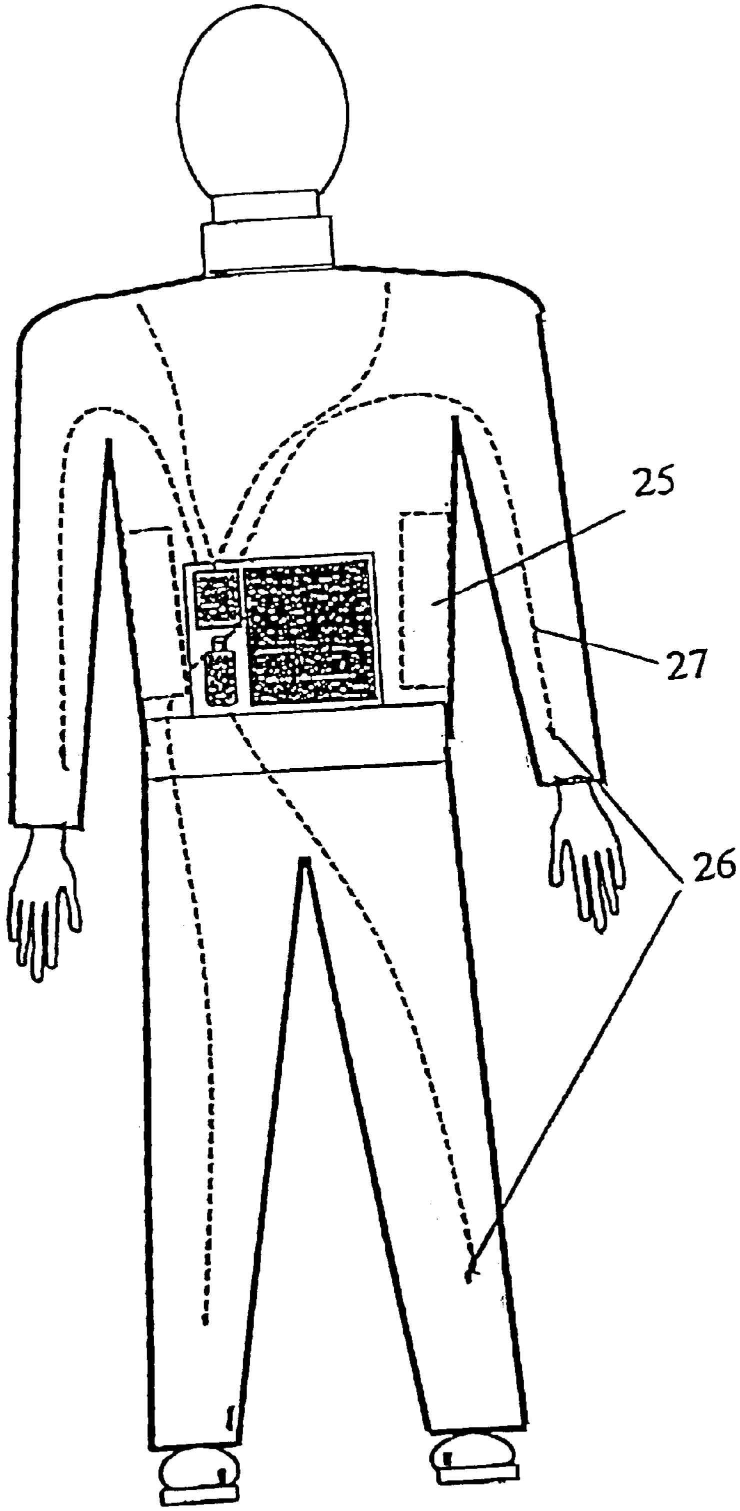
FIGS. 7 and 7A (hereinafter FIG. 7) are a showing location of the temperature sensors and related signal lines, and moisture absorbing pads.
Figure 7A:
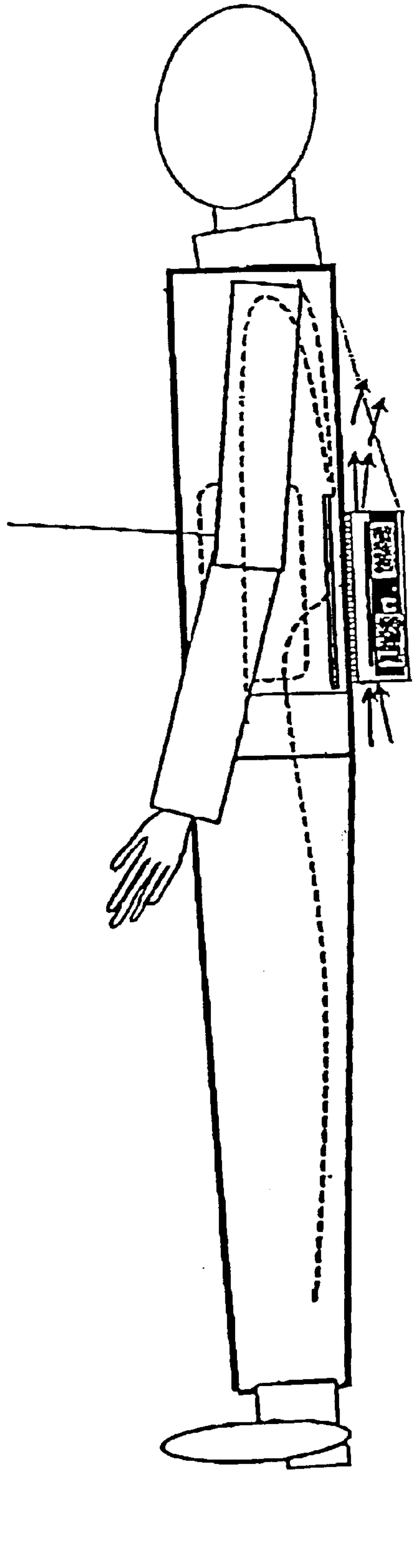

By splitting the whole fluid circulating system into sections individually controlled by separate valves, independent temperature control of different parts of the body is feasible. The heat transfer fluid circulation might be forced by different means. An option is a fluid pumping system, applying diaphragm pumps 31, located in shoes (between heel and shoe) as shown in FIG. 6 and activated by walking. Another solution is thermally induced flow (thermal convection) or the micro-pump.

Temperature Control System

Another important feature of the heating suit is temperature control system and moisture adsorption system. The temperature control system as shown in FIG. body. These sensors measuring local temperatures, via control system module, activate the relevant control shutters 15 or valves 17, that regulate the stream of energy delivered to the specified body part.

The control system (apparatus) comprise electronic circuits to which the temperatures are applied as control signals and transducers attached to the shatters or adjustable control valves provide for heat distribution. The temperature reading system comprise of sensors for temperature sensing, signal lines for signal transfer and multi-point reading and signal processing electronic module for signal processing and steering signals sending.

Moisture Adsorption System

Yet another object of the invention is to provide for moisture absorption. During physical activity significant amount of moisture (sweet) inside of the suit is generated and require to be removed. Additional feature of the heating suit according to this invention is moisture absorption pad that removes excessive moisture from the suit interior to keep a person dry and comfortable underneath. Moisture absorption pads are based on polymers characterized by a very high water absorption capacity. The pads are located in separate pockets of the suit and are accessible easily through the zipper locks for replacement after saturation.

It is believed that person skilled in the art will make obvious modifications in the preferred embodiments of this invention as shown in the drawings and described hereinabove without departing from the scope of the following claims. Specifically, various combinations of the elements of applicant's system may be made as claimed.

What is claimed is:

1. A heating suit for keeping a human body warm under cold weather conditions, comprising:

a heat insulated suit with infrared transparent window;

a light, portable, low temperature, infrared heater located outside of the suit;

a heat collector located inside of the suit to collect heat radiated from the infrared heater through the infrared transparent window; and a heat distribution system to deliver heat collected by the heat collector to different parts of the suit.

2. The heating suit according to claim 1, wherein the heat distribution system includes heat flux control elements to independently control heat distribution to different parts of the suit, whereby the wearer selectively directs more heat to selected parts of the suit as required.

3. The heating suit according to claim 1 wherein the heat distribution system includes temperature sensors coupled to heat flux control elements, whereby heat is distributed to parts of the suit to maintain a selected temperature setting for a selected one of the heat flux control elements.

4. The heating suit according to claim 1 wherein the infrared heater is a catalytic burner.

5. The heating suit according to claim 1, wherein a plate is positioned in the infrared transparent window, thereby enhancing heat transfer efficiency.

6. The heating suit according to claim 1 wherein the heat distribution system is an optical system that directs the infrared radiation to different parts of the suit.

7. The heating suit according to claim 1, wherein the optical heat distribution system consists of plurality of flexible infrared optic fibres each having a first end and a second end, the first end being in communication with the heat collector and the second end distributing heat to different parts of the suit.

8. The heating suit according to claim 7, wherein an infrared micro-heater is attached to the second end of each of the optic fibres.

9. The heating suit according to claim 1 wherein the collector has a surface covered with a infrared radiation adsorbing layer, whereby heat radiated from the infrared heater through the infrared transparent window is adsorbed.

10. The heating suit according to claim 1, wherein the collector is in the form of a heat exchanger and the heat distribution system includes fluid circulation through the heat exchanger thereby effecting a heat exchange.

11. The heating suit according to claim 1 wherein the collector includes a heat exchanger located inside of the suit and connected by fluid circulation pipes to the infrared heater located outside of the suit.

12. The heating suit according to claim 1, wherein a heat exchanger is located outside of the suit and connected by fluid circulation pipes to the heat distribution system.

13. The heating suit according to claim 10, wherein fluid circulation is effected by pumps.

14. The heating suit according to claim 13, wherein the pumps are diaphragm pumps.

15. The heating suit according to claim 14, wherein the diaphragm pumps are located in shoes and activated by walking.

16. The heating suit according to claim 1, wherein the heat distribution system includes temperature sensors connected via temperature signal lines to an electronic temperature control module and a series of heat flux control elements connected to the electronic temperature control module, whereby selected temperatures for different parts of the suit are maintained.

17. The heating suit according to claim 1, wherein a heat exchanger located outside of the suit and recovers heat from exhaust gases from the infrared heater.

18. The heating suit according to claim 1, wherein air is passed through a heat exchanger to a plurality of air channels providing heat delivery to head gear for the suit.

19. The heating suit according to claim 1, wherein moisture absorbtion pads containing highly adsorbing materials are located within the suit to absorb excess moisture.

20. The heating suit according to claim 19, wherein the moisture absorbtion pads are made from polyacrylamid.

21. A heating suit for keeping a human body warm under cold weather conditions, comprising:

a heat insulated suit with infrared transparent window;

a light, portable, low temperature, infrared heater located outside of the suit;

a heat collector located inside of the suit to collect heat radiated from the infrared heater through the infrared transparent window;

a plate being positioned in the infrared transparent window, thereby enhancing heat transfer efficiency and a heat distribution system to deliver heat collected by the heat collector to different parts of the suit, the heat distribution system is an optical system that includes a plurality of flexible infrared optical fibres that direct the infrared radiation to different parts of the suit, each of the plurality of flexible infrared optic fibres having a first end and a second end, the first end being in communication with the heat collector and the second end being attached to an infrared micro-heater;

the heat distribution system including heat flux control elements to independently control heat distribution to different parts of the suit, whereby the wearer selectively directs more heat to selected parts of the suit as required.

22. The heating suit according to claim 21, wherein the heat distribution system includes temperature sensors connected via temperature signal lines to an electronic temperature control module, the heat flux control elements being connected to the electronic temperature control module, whereby selected temperatures for different parts of the suit are maintained.

23. The heating suit according to claim 21, wherein the infrared heater is a catalytic burner.

24. The heating suit according to claim 21, wherein a heat exchanger located outside of the suit recovers heat from exhaust gases the infrared heater.

25. The heating suit according to claim 24, wherein air is passed through a heat exchanger to a plurality of air channels providing heat delivery to head gear for the suit.

26. The heating suit according to claim 21, wherein moisture absorbtion pads containing highly adsorbing materials are located within the suit to absorb excess moisture.

27. The heating suit according to claim 26, wherein the moisture absorbtion pads are made from polyacrylamid.

28. A heating suit for keeping a human body warm under cold weather conditions, comprising:

a heat insulated suit with infrared transparent window;

a light, portable, low temperature, infrared heater located outside of the suit;

a heat collector located inside of the suit to collect heat radiated from the infrared heater through the infrared transparent window, the collector being in the form of a heat exchanger and having a surface covered with a infrared radiation adsorbing layer, whereby heat radiated from the infrared heater through the infrared transparent window is adsorbed;

a plate being positioned in the infrared transparent window, thereby enhancing heat transfer efficiency;

a heat distribution system to deliver heat collected by the heat collector to different parts of the suit, the heat distribution system having fluid circulation through the heat exchanger thereby effecting a heat exchange, fluid circulation being effected by diaphragm pumps incorporated into the suit such that the diaphragm pumps are activated as a wearer of the suit moves; and the heat distribution system including heat flux control elements to independently control heat distribution to different parts of the suit, whereby the wearer selectively directs more heat to selected parts of the suit as required.

29. The heating suit according to claim 28, wherein the heat distribution system includes temperature sensors connected via temperature signal lines to an electronic temperature control module, the heat flux control elements being connected to the electronic temperature control module, whereby selected temperatures for different parts of the suit are maintained.

30. The heating suit according to claim 28, wherein the infrared heater is a catalytic burner.

31. The heating suit according to claim 28, wherein moisture absorbtion pads containing highly adsorbing materials are located within the suit to absorb excess moisture.

32. The heating suit according to claim 31, wherein the moisture absorbtion pads are made from polyacrylamid.

33. The heating suit according to claim 28, wherein the heat exchanger is connected by fluid circulation pipes to the infrared heater located outside of the suit.

34. The heating suit according to claim 28, wherein a secondary heat exchanger is located outside of the suit and connected by fluid circulation pipes to the heat distribution system.

35. The heating suit according to claim 28, wherein a tertiary heat exchanger located outside of the suit recovers heat from exhaust gases from the infrared heater.

36. The heating suit according to claim 35, wherein air is passed through the tertiary heat exchanger to a plurality of air channels providing heat delivery to head gear for the suit.

37. The heating suit according to claim 28, wherein the diaphragm pumps are located in shoes and activated by walking.

* * * * *